(12) United States Patent  
Hartz

(10) Patent No.: US 6,558,627 B1  
(45) Date of Patent: May 6, 2003

(54) TEMPERATURE CONTROL APPARATUS AND METHOD FOR PIPETTING ROBOT

(75) Inventor: Detlef Hartz, Frankfurt (DE)

(73) Assignee: Aventis Pharma Deutschland GmbH, Frankfurt am Main (DE)

( * ) Notice: Subject to any disclaimer, the term of this patent is extended or adjusted under 35 U.S.C. 154(b) by 0 days.

(21) Appl. No.: 09/129,784

(22) Filed: Aug. 6, 1998

(30) Foreign Application Priority Data

Aug. 8, 1997 (DE) .................................. 297 14 206 U  
Apr. 15, 1998 (DE) .................................. 198 16 424

(51) Int. Cl.⁷ ................................................. B01L 7/00
(52) U.S. Cl. ........................ 422/99; 422/63; 422/100; 422/102; 422/104; 435/288.4; 435/303.1; 436/43; 436/174; 436/180
(58) Field of Search ................... 422/63, 100, 102, 422/104, 99; 436/43, 174, 180; 435/288.3, 288.4, 303.1

(56) References Cited

U.S. PATENT DOCUMENTS 4,058,370 A * 11/1977 Suovaniemi ................. 422/64
4,682,891 A * 7/1987 De Macario et al ........ 356/244
4,919,894 A * 4/1990 Daniel ......................... 422/104
5,055,408 A   10/1991 Higo et al. ..................... 436/48
5,061,630 A * 10/1991 Knopf et al. ................ 435/290
5,073,346 A * 12/1991 Partanen et al. .............. 422/99
5,443,791 A    8/1995 Cathcart et al. .............. 422/65
5,455,008 A   10/1995 Earley et al. ................. 422/100
5,475,610 A * 12/1995 Atwood et al.

FOREIGN PATENT DOCUMENTS

| DE | 40 03 604 A1 | 8/1991 |
| EP | 0 339 710 | 11/1989 |
| EP | 0 500 506 A1 | 8/1992 |
| WO | 91/12516 * | 8/1991 |

* cited by examiner

Primary Examiner—Jan Ludlow  
(74) Attorney, Agent, or Firm—Finnegan, Henderson, Farabow, Garrett and Dunner, L.L.P.

(57) ABSTRACT

A temperature control apparatus in the form of a plate is provided for pipetting robots, the plate having a spiral tube for a temperature control medium and which apparatus is divided into at least two segments for holding microtitration plates. A pipetting robot which utilizes a maximum amount of its working space, increasing the efficiency of pipetting liquids for analysis, is also provided.

8 Claims, 4 Drawing Sheets

TEMPERATURE CONTROL APPARATUS AND METHOD FOR PIPETTING ROBOT

BACKGROUND OF THE INVENTION

1. Field of the Invention

The present invention relates to a temperature control apparatus for pipetting robots for holding microtitration plates.

2. Description of the Prior Art

Temperature control apparatus for pipetting robots are known. For example, Beckmann Instruments GmbH, Frankfurter Ring 116, D-80810 Munich markets pipetting robots under the name BIOMEK 2000. Such robots are used in the pharmaceutical industry, for example, for screening unknown substances (screening tests). They comprise temperature control apparatus for containers for the unknown substances, which are arranged on microtitration plates, as well as for pipetting apparatus, which can be actuated via programming languages or program codes, for filling these containers.

The temperature control apparatus are used to keep the unknown substances at a constant temperature during the pipetting process in the screening tests. The temperatures of known temperature control apparatus can be controlled by means of Peltier elements. That is, they can be heated or cooled, and they have two segments for holding microtitration plates.

Disadvantages of known temperature control apparatus are that they are suitable only for microtitration plates of a specific format, and that they do not fully utilize the available working area of the pipetting robot, or the full area which the pipetting apparatus can reach. For example, as shown in FIG. 3B, a zone 20 of working area 15 is not utilized during a conventional pipetting process. The standard program for pipetting robots does not recognize zone 20, and therefore, the full working area 15 of the pipetting robot is not utilized. This means that microtitration plates 14, held in place by taps 21, must be of a specific format to fit within the robot-recognized areas of working area 15.

SUMMARY OF THE INVENTION

Accordingly, the present invention is directed to an apparatus for controlling temperature which provides advantages and obviates a number of problems in known temperature control apparatus.

To achieve the objects and in accordance with the purpose of the invention, as embodied and broadly described herein, the invention includes a temperature control apparatus including a plate having a spiral tube therein for receiving a temperature-control medium, wherein the plate is divided into at least two segments for holding microtitration plates.

According to another aspect of the present invention, the invention includes temperature control apparatus for pipetting robots including a plate having a spiral tube therein for receiving a temperature-control medium, wherein the plate is divided into at least two segments for holding microtitration plates, wherein the plate includes an upper part and a lower part, and wherein both the upper and lower parts are rectangular, the upper part resting on top of the lower part. The upper part includes grooves in an upper surface thereof, which is facing away from the lower part, the grooves dividing the surface into at least two segments for holding microtitration plates.

According to a further aspect of the present invention, the invention includes a temperature control apparatus including a plate having a spiral tube therein for receiving a temperature-control medium, wherein the plate is divided into at least two segments for holding microtitration plates, wherein the plate includes an upper part and a lower part, and wherein both the upper and lower parts are rectangular, the upper part resting on top of the lower part. The lower part includes a channel in an upper surface of the lower part, which is in contact with the upper part, wherein the channel forms a spiral tube in the assembled state. The upper part and lower part can be, connected to one another by normal fastening means.

According to another aspect of the present invention, the present invention includes a programmable pipetting robot having a temperature control apparatus including a plate having a spiral tube therein for receiving a temperature-control medium, wherein the plate is divided into at least two segments for holding microtitration plates, a working area containing the at least one temperature control apparatus, one microtitration plate holding containers for liquids located on each segment of the temperature control apparatus, a pipefting apparatus, and means for recognizing the position of each microtitration plate, wherein the pipetting robot is programmed such that, when the temperature-control apparatus and the microtitration plates are arranged correctly, the robot recognizes and fills each of the containers with a liquid.

According to another aspect of the present invention, the invention includes a method of automatically pipetting fluids into wells of microtitration plates resting on a temperature control apparatus in a working area of a pipetting robot, including defining the working area of the robot to include an entire working table surface, placing microtitration plates in at least the middle of the working area, inputting a fluid source position, inputting a fluid destination position within the middle of the defined working area, moving a pipetting apparatus to the destination position, and filling a well of a microtitration plate located at the destination position.

Additional objects and advantages of the invention will be set forth in part in the description which follows, and in part will be obvious from the description, or may be learned by the practice of the invention. The objects and advantages of the invention no will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrates one embodiment of the invention and together with the description, serve to explain the principles of the invention.

DESCRIPTION OF THE PREFERRED EMBODIMENT

Reference will now be made in detail to the present preferred embodiment of the invention, an example of which is illustrated in the accompanying drawings. Whenever possible, the same reference numbers will be used throughout the drawings to refer to the same or like parts.

Figure 1:
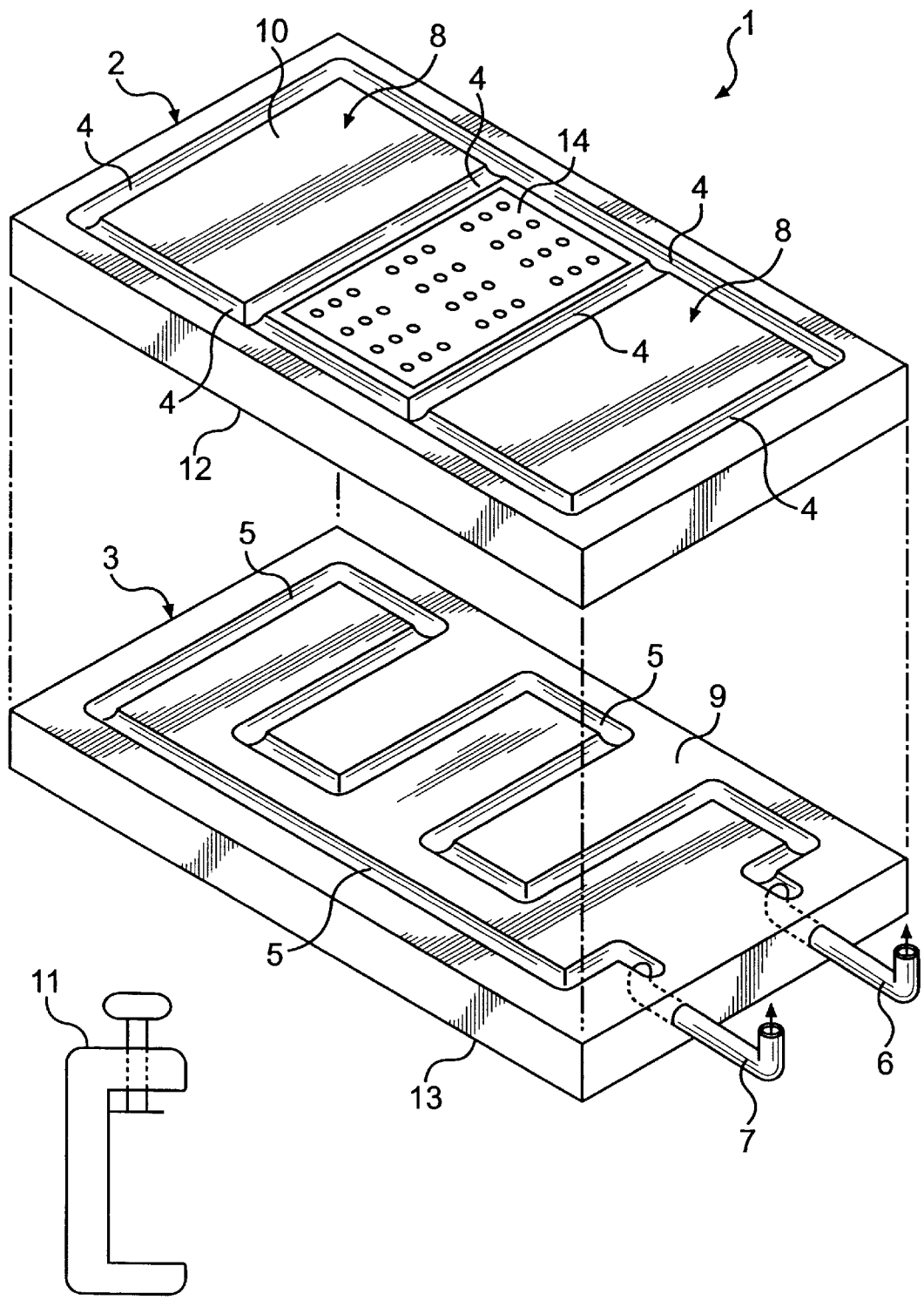
FIG. 1 is a perspective view of the temperature control device according to the present invention.

The preferred embodiment of the temperature control apparatus is illustrated in perspective in FIG. 1. Temperature control apparatus 1 includes an upper part 2 and a lower part 3, each of which is formed as a rectangular plate, the plates being connectable by any common fastening element, such as a screw or a clamp 11. Temperature control apparatus 1 may be made from any suitable material which will support microtitration plates 14 and which can support a temperature control medium. Examples of suitable materials are plastics and metals.

Lower part 3 includes an upper surface 9 and a lower surface 13. Upper surface 9 of lower part 3 includes a spiral channel which, in the assembled state, forms a spiral tube 5. The spiral tube 5 includes an input 6 and an output 7 for receiving a heating or cooling medium, depending on the operation to be performed.

Upper part 2 includes an upper surface 10 and a lower surface 12. Grooves 4 are incorporated in upper part 2, in upper surface 10 which is facing away from lower part 3, such that surface 10 is divided into three segments 8 for holding microtitration plates 14. A different division into two, or more than three, segments 8 is possible without further ramifications.

Figure 2:
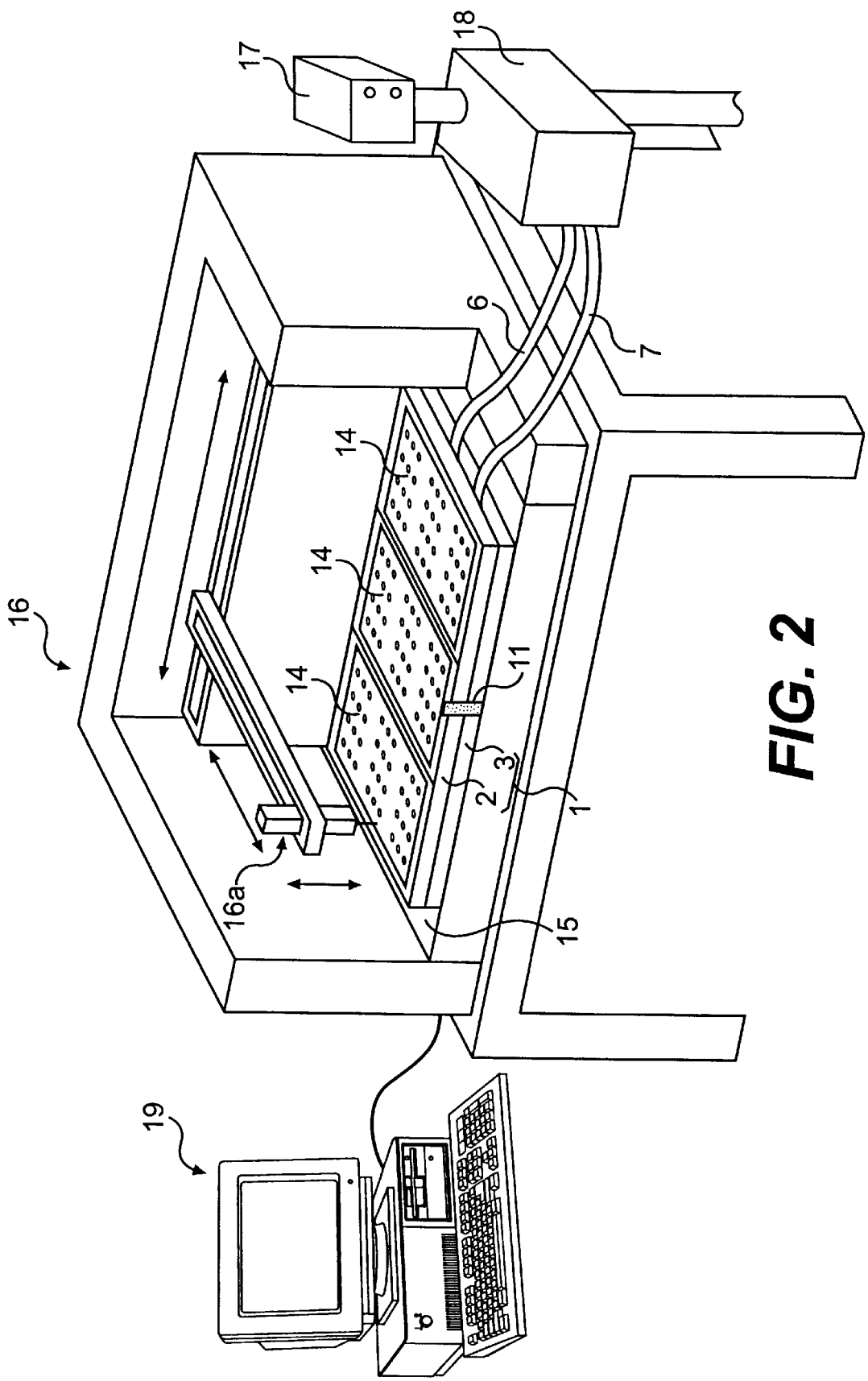
FIG. 2 is a perspective view of a pipetting robot utilizing the temperature control device of FIG. 1 according to the present invention.
Figure 3A:
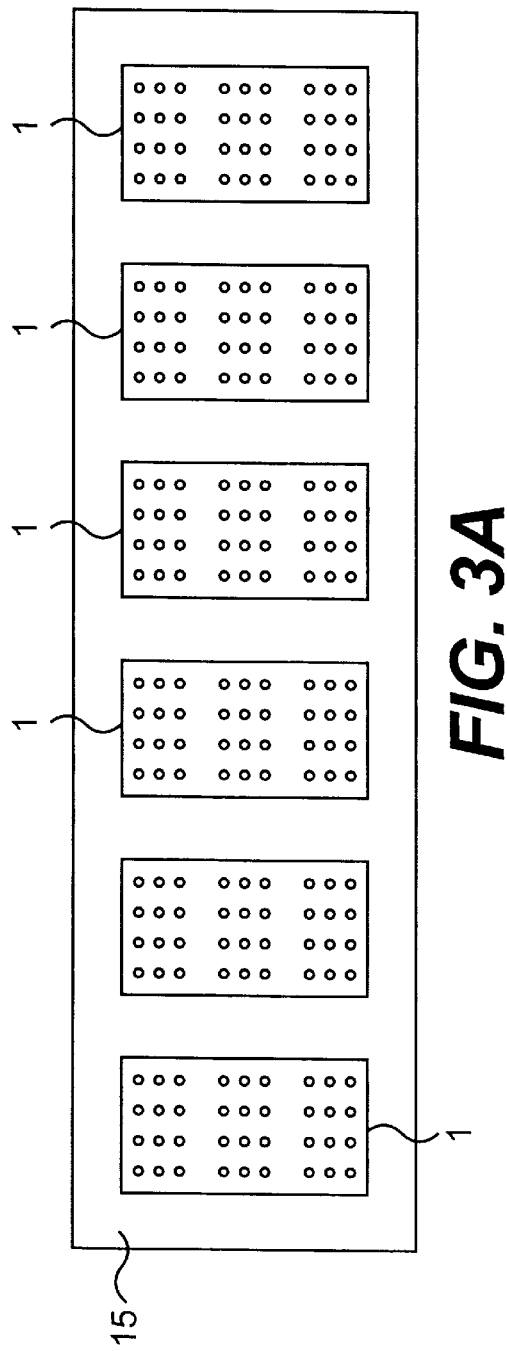
FIG. 3A is a top view of microtitration plates placed in a utilized working area of a pipetting robot according to the present invention.

The rectangular plates, when assembled, rest one on top of the other to form the temperature control apparatus 1. When assembled, lower surface 12 of upper part 2 rests on top of upper surface 9 of lower part 3. As shown in FIG. 2, microtitration plates 14 fit between grooves 4 into segments 8, and rest on upper surface 10 of upper part 3. As shown in FIG. 3A, temperature of the microtitration plates 14 is monitored once they are placed on the temperature control apparatus via a thermostat 17 monitoring the temperature of a heating or cooling medium flowing in spiral channel 5 through temperature control apparatus 1. The heating or cooling medium is contained in container 18 and flows from container 18 into input 6, through temperature control apparatus 1, out of output 7, and returns to container 18 where the temperature of the temperature control medium is measured by thermostat 17. Once a desired temperature is reached, the thermostat is set, and pipetting robot 16 can fill the wells of microtitration plates 14.

Figure 3B:
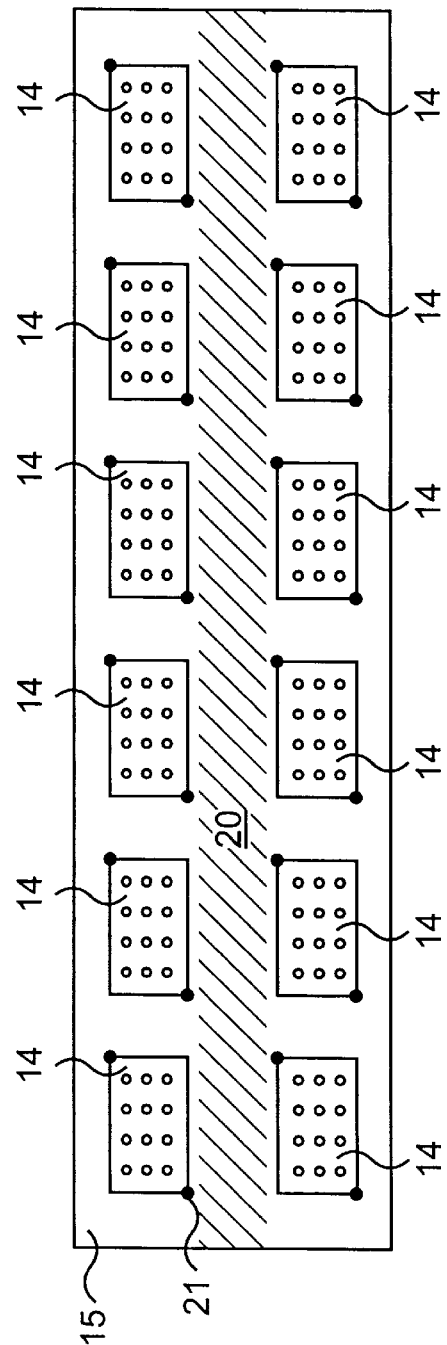
FIG. 3B is a top view of microtitration plates placed in a utilized working area of a pipetting robot according to the prior art.
Figure 4:
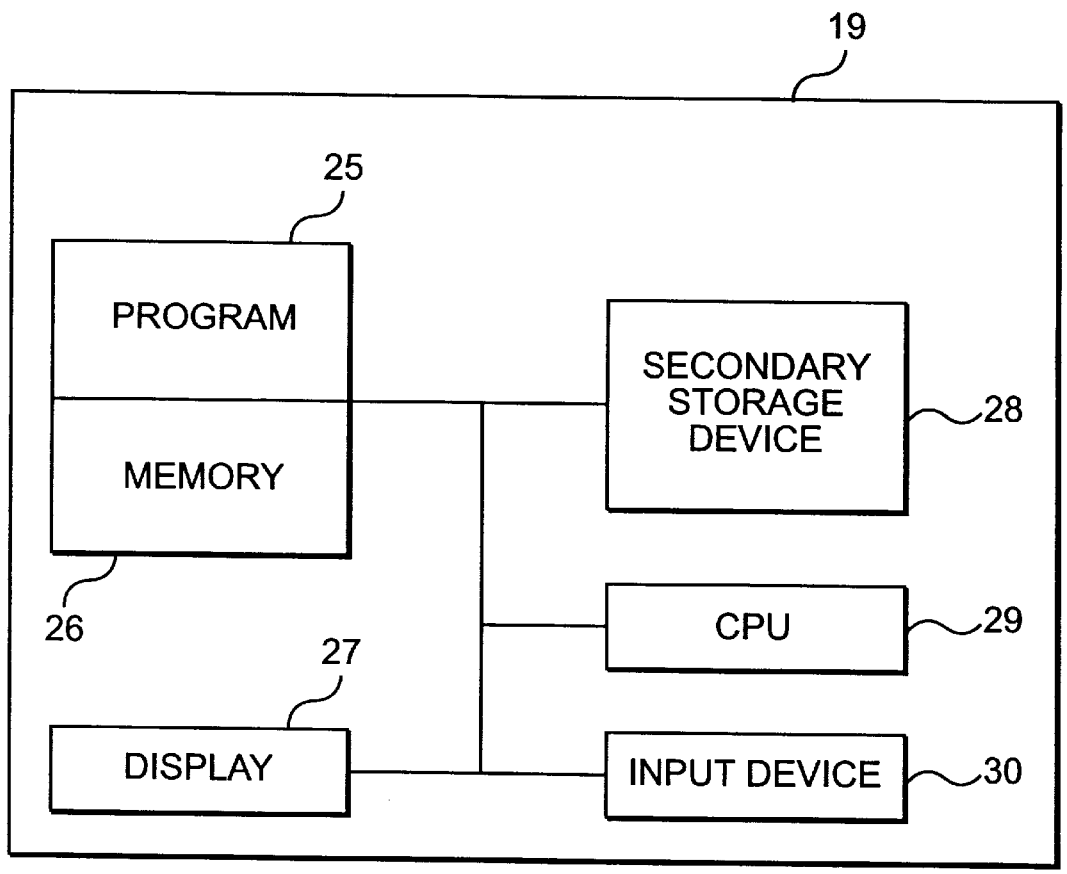
FIG. 4 is a block diagram of a computer system in which interfaces consistent with the present invention may be implemented.

According to one aspect of the invention and as embodied in FIG. 2, the present invention includes a pipetting robot. Conventional pipetting robots are restricted in their access to the available working area 15. Standard programs for pipetting robots utilizing conventional temperature control devices fix positions reachable by the pipetting robot in the horizontal plane. For example, as shown in FIG. 3B, a conventional pipetting robot cannot access zone 20 of working area 15. In a conventional working space, where there are twelve positions defined to receive microtitration plates, each microtitration plate generally containing 96 wells.

Pipetting robot 16, as embodied herein and shown in FIG. 2, includes a working area 15, a pipetting apparatus 16a, a temperature control apparatus 1 (comprising elements 2 and 3), a controller 19, a thermostat 17, and a container 18 for holding a temperature control medium.

Pipetting apparatus 16a is moveable in three dimensions. Pipetting apparatus 16a is moveable longitudinally along working space 15, it is moveable horizontally across the width of temperature control apparatus 1, and it is moveable vertically. Controller 19 includes a microprocessor, such as a computer.

Pipetting robot 16 may access and utilize additional portions of the work space 15 when additional programming is performed. Thus, in contrast to conventional robots and as shown in FIG. 3A, the working area of the pipetting robot of the present invention may hold six temperature control apparatus 1, and therefore the working area contains a total of 18 positions defined to receive microtitration plates, each microtitration plate generally containing 96 wells. Thus, the present invention allows a 33% increase in the amount of working area available for use.

An example of a program for actuation of a pipetting robot according to the invention is described in the following text. This program is executable in a memory 26, a display 27, a secondary storage device 28, a CPU 29, and an input device 30. This program was written in the programming language TCL, which is proposed by the Beckmann company for such applications and is accessible via the Internet.

```
#    Universal - TCL - Script for once-outputting of volumes.

#    When defining local variables, please observe upper
#    case/lower case!!!
#    -----------------------------------------------------
#        Should a Tip_touch be made
#        and if yes, where?
#        Only source, only destination or both
#        1 = Yes/0 = No
#    -----------------------------------------------------
set source_tip_touch 1
set taget_tip_touch 1
#    -----------------------------------------------------
#        The desired volumes are used from here on
#    -----------------------------------------------------

set disp_vol 100
set bias_vol 10

#    if deliver_vol then no blow_out

set deliver_vol 15

#    blowout = 0 no blowout!!

set blowout_vol 0

#    calculate volume to be accommodated if greater than m_vol then
#    terminate the script

if {$deliver_vol > 1 } {set blowout_vol 0}
if {$blowout_vol > 1 } {set deliver_vol 0}
set asp_vol [expr $disp_vol+$bias_vol+$deliver_vol+$blowout_vol]

#    -----------------------------------------------------
#            Pipette parameters used from here on
#    -----------------------------------------------------
#    Depending on the pipette used
#    MP200 slope: 0.0838/offset: 0.05/m_vol 240
set m_vol 240
```

-continued

```
set slope 0.0838
set offset 0.05

# --------------------------------------------------------
#    The coordinates for the source container are used from here on
# --------------------------------------------------------

#    Source: MPT to Position B3
set source_x 77050
set source_y 41401
set source_certain_move 32000
set source_asp_high 30700
set source_disp_high 31000
set source_touch_x 450
set source_touch_high 31200

# --------------------------------------------------------
#    The coordinates of the destination vessel are used from here on
# --------------------------------------------------------

#    Destination: Deep Well at Position A4
set target_x 90960
set target_y 26201
set target_sicher_move 32300
set target_disp_high 31000
set target_touch_x 450
set target_touch_high 31600

# --------------------------------------------------------
#    No more changes may be made from this point !!!
# --------------------------------------------------------

set certain_move [expr $source_certain_move*1]
if {$source_certain_move < $target_certain_move}
{set certain_move [expr $target_certain_move*1]}

#    Convert to BIOMEK coordinates

set BIAS [expr int((($bias_vol*100*$slope+($offset*100))+0.5*-1)]
set DISPENSE [expr int((($disp_vol*100*$slope+($offset*100))+0.5*-1)]
set DELIVER 0
if {$deliver_vol > 1}
{set DELIVER [expr int((($deliver_vol*100*$slope+($offset*100))+0.5*-1)]
set BLOWOUT 0
set GET_BLOWOUT 0
if {$blowout_vol > 1}
{set BLOWOUT [expr int((($blowout_vol*100*$slope+($offset*100))+0.5*-1)]
set GET_BLOWOUT [expr abs($BLOWOUT)]}
set ASPIRATE [exp abs($DISPENSE+abs($BIAS)+abs($DELIVER)]

#    set speed up

SX 650
SY 650

#    move to destination labware

MA 0 0 $certain_move
if {$blowout_vol > 1} {MT $GET_BLOWOUT}
MA $source_x $source_y 0
MA 0 0 $source_asp_high

#    get volume

MS TT 11 20 0
MT $ASPIRATE
MS TT 11 20 0
MT $BIAS
if {$source_tip_touch > 0}
{MA 0 0 $source_touch_high
MS TT 11 10 0
MV $source_touch_x 0 0
MS TT 11 20 0
MV [expr $source_touch_x*-1]0 0}
MA 0 0 $certain_move
```

```

#    move to source

MA $target_x $target_y 0
MS TT 11 10 0
MA 0 0 $target_disp_high
MS TT 11 20 0
MT $DISPENSE
if {$blowout_vol >0} {MT $BLOWOUT}
if {$target_tip_touch > 0}
{MA 0 0 $target_touch_high
MS TT 11 10 0
MV $target_touch_x 0 0
MS TT 11 20 0
MV [expr $target_touch_1_x*-1]0 0}
MS TT 11 10 0
MA 0 0 $certain_move
MA $source_x $source_y 0
if {$deliver_vol > 0}
{MS TT 11 10 0
MA 0 0 $source_disp_high
MT $DELIVER
MS TT 11 10 0
if {$source_tip_touch > 0}
{MA 0 0 $source_touch_high
MS TT 11 10 0
MV $source_touch_x 0 0
MS TT 11 20 0
MV [expr $source_touch_x*-1]0 0}}
MA 0 0 $certain_move

#    speed down

SX 500
SY 500

#    Clear all initialized variables

unset source_tip_touch
unset target_tip_touch
unset disp_vol
unset bias_vol
unset deliver_vol
unset blowout_vol
unset asp_vol
unset m_vol
unset slope
unset offset
unset source_x
unset source_y
unset source_certain_move
unset source_asp_high
unset source_disp_high
unset source_touch_x
unset source_touch_high
unset target_x
unset target_y
unset target_certain_move
unset target_disp_high
unset target_touch_x
unset target_touch_high
unset certain_move
unset BIAS
unset DISPENSE
unset DELIVER
unset BLOWOUT
unset GET_BLOWOUT
unset ASPIRATE
```

Use of the above program, or similar programming, allows pipetting robot 16 to access all wells in all microtitration plates 14 which are within pipetting robot's 16 working space 15. Utilizing such a program with pipetting robot 16, which is controlled by a microprocessor, such as computer 19, allows more efficient processing of materials to be analyzed.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A temperature control apparatus for pipetting robots for holding microtitration plates, comprising:

a plate having first and second pieces forming upper and lower parts, respectively, a serpentine tube within the plate being configured to receive a temperature-control medium and being defined by the upper and lower parts of the plate, the plate including at least two defined segments for holding microtitration plates.

2. The temperature control apparatus of claim 1, wherein both the upper and lower parts are rectangular, the upper part resting on top of the lower part; and wherein the upper part includes grooves in an upper surface thereof, which is facing away from the lower part, said grooves dividing the upper surface to define the at least two segments for holding microtitration plates.

3. The temperature control apparatus of claim 1, wherein both the upper and lower parts are rectangular, the upper part resting on top of the lower part; and wherein the upper part includes grooves in an upper surface thereof, which is facing away from the lower part, said grooves dividing the upper surface to define at least three segments for holding microtitration plates.

4. The temperature control apparatus of claim 1, wherein the plate includes at least three defined segments for holding microtitration plates.

5. The temperature control apparatus of claim 1, wherein both the upper and lower parts are rectangular, the upper part resting on top of the lower part; and wherein the lower part includes a channel in an upper surface of the lower part, which is in contact with the upper part, wherein the channel forms the serpentine tube when the upper part of the plate is resting on the lower part.

6. The temperature control apparatus of claim 1, wherein both the upper and lower parts are rectangular, the upper part resting on top of the lower part;

wherein the upper part includes grooves in an upper surface thereof, which is facing away from the lower part, said grooves dividing the upper surface to define at least three segments for holding microtitration plates; and wherein the lower part includes a channel in an upper surface of the lower part, which is in contact with the upper part, wherein the channel forms the serpentine tube when the upper part of the plate is resting on the lower part.

7. A pipetting robot, comprising:

a working area;

a pipetting apparatus;

at least one microtitration plate; and a temperature control apparatus including a plate having first and second pieces forming upper and lower parts, respectively, a serpentine tube within the plate being configured to receive a temperature-control medium and being defined by the upper and lower parts of the plate, wherein the plate includes at least two defined segments for holding microtitration plates.

8. A programmable pipetting robot, comprising:

at least one temperature control apparatus including a plate having first and second pieces forming upper and lower parts, respectively, a serpentine tube within the plate being configured to receive a temperature-control medium and being defined by the upper and lower parts of the plate, wherein the plate includes at least two defined segments for holding microtitration plates;

a working area containing the at least one temperature control apparatus;

one microtitration plate holding containers for liquids located on each segment of the temperature control apparatus;

a pipetting apparatus; and a controller for recognizing the position of each microtitration plate, wherein the pipetting robot is programmed such that, when the temperature-control apparatus and the microtitration plates are arranged correctly, the robot recognizes and fills each of the containers with a liquid.

* * * * *